United States Patent [19]

Devaney, Jr. et al.

[11] Patent Number: 4,877,586
[45] Date of Patent: Oct. 31, 1989

[54] SLIDING TEST DEVICE FOR ASSAYS

[75] Inventors: Mark J. Devaney, Jr.; Edward H. Wannenwetsch, both of Rochester, N.Y.

[73] Assignee: Eastman Kodak Company, Rochester, N.Y.

[21] Appl. No.: 224,831

[22] Filed: Jul. 27, 1988

[51] Int. Cl.$^4$ .................. B01L 11/00; G01N 31/22
[52] U.S. Cl. ........................ 422/101; 422/58
[58] Field of Search ...................... 422/56–58, 422/61, 68, 69, 101; 436/177, 178, 518, 824; 435/7, 805, 808; 210/282, 447

[56] References Cited

U.S. PATENT DOCUMENTS

| | | | |
|---|---|---|---|
| 3,888,629 | 6/1975 | Bagshawe | 422/61 |
| 4,246,339 | 1/1981 | Cole et a. | 422/101 |
| 4,734,262 | 3/1988 | Bagshawe | 422/101 |

Primary Examiner—Barry S. Richman
Assistant Examiner—William H. Beisner
Attorney, Agent, or Firm—Dana M. Schmidt

[57] ABSTRACT

An improved test device, useful in conducting reactions, which comprises (a) a well lconfigured to confine temporarily a liquid patient sample admixed with at least one reagent, such as an immunoreagent, to conduct such a reaction, (b) a filter at the bottom of the well with pores effective to pass free, unreacted reagent but not reacted or complexed reagent, and (c) an absorbent material underneath the filter effective to draw off liquid in the well after the reaction. The device further includes (d) a non-absorbent pad underneath the filter, adjacent to the absorbent material, and (e) means for moving the filter and the absorbent material relative to each other, and the filter and the pad relative to each other, between two positions, one in which the filter contacts the non-absorbent pad and the other in which the filter contacts the absorbent material.

13 Claims, 5 Drawing Sheets

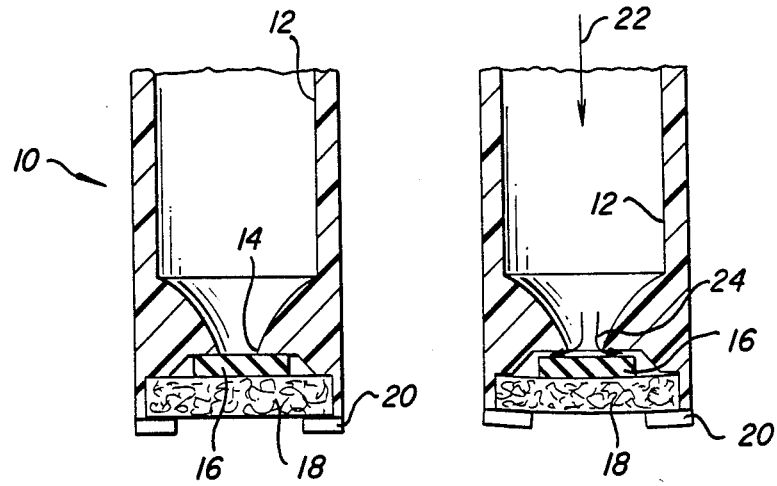
Fig. 1A (PRIOR ART)
Fig. 1B (PRIOR ART)
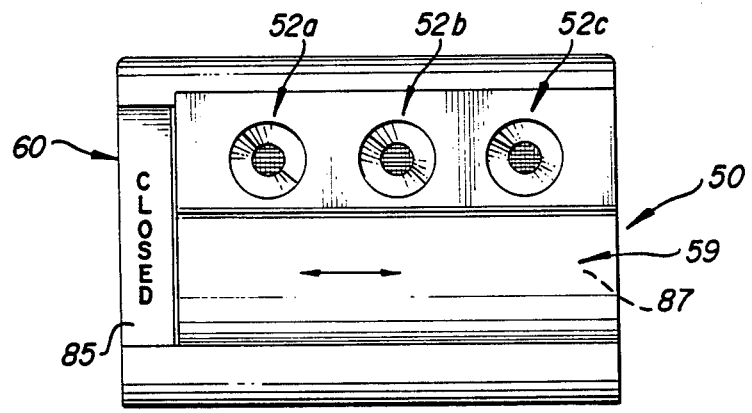
Fig. 2

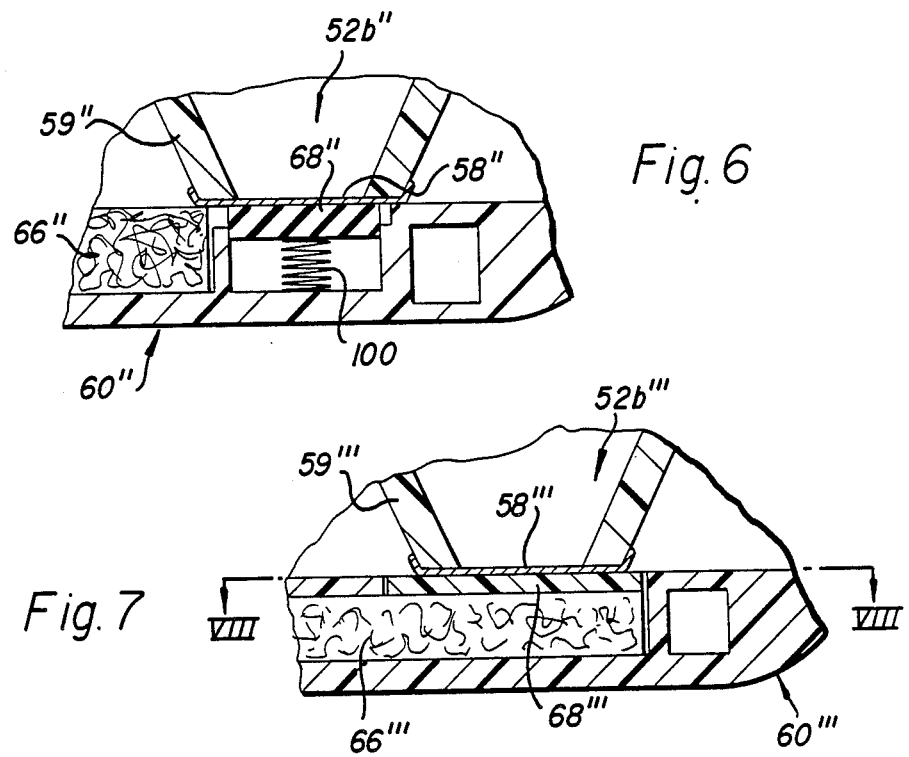
Fig. 6
Fig. 7
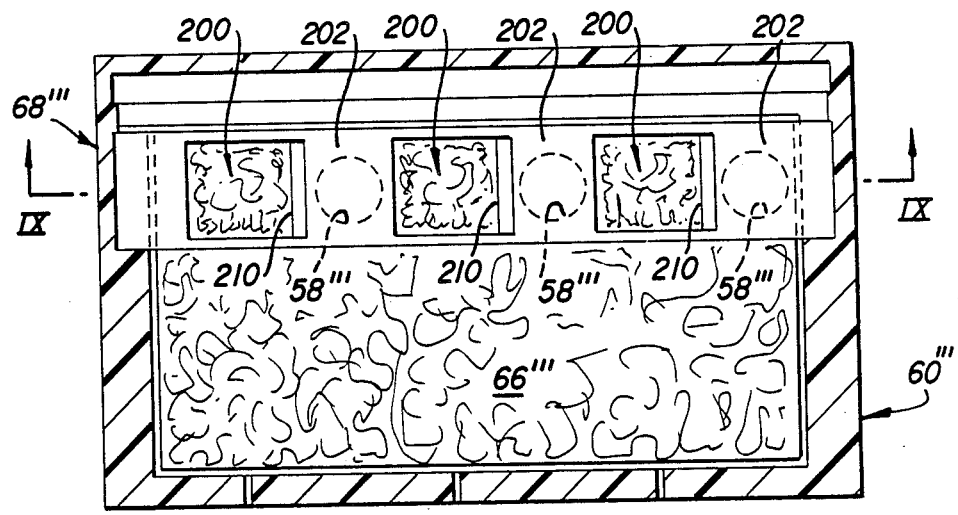
Fig. 8

SLIDING TEST DEVICE FOR ASSAYS

FIELD OF THE INVENTION

This invention relates to a construction of a test device that allows it to alternate between no-liquid flow, and liquid flow, through a filter, the filter being used to separate a reaction product from the reagents that provide the reaction product.

BACKGROUND OF THE INVENTION

Diagnostic devices have been provided in the past for conducting immunoreactions in one or more test wells to determine the qualitative existence of pregnancy or an infectious disease. Such devices commonly include a filter membrane at the bottom of the well to separate out free, unreacted immunoreagents, from complexed immunoreagents. (The former pass through the membrane.) Underneath such membranes is preferably located on absorbent material to absorb the liquid of the reaction mixture. It has been conventional in such devices to provide for control of liquid flow, so as to first retain the liquid in the well above the membrane for an incubation period, and then to allow flow through the membrane. Previously provided mechanism for controlling the flow include an aperture in the housing for the absorbent material underneath, and seals for opening and closing the aperture. When the aperture is open, normal liquid wetting causes the liquid to flow though the membrane into the absorbent material. Such seals, although effective, require careful tolerances and assembly techniques, so as to insure the apertures are normally closed, while at the same time are openable using manual forces easily available to the user.

Thus, prior to this invention there has been a need to provide liquid flow control for such devices that do not have such high tolerance requirements, while at the same time allowing easy use by the operator.

A recent development towards this end is that described in U.S. Pat. No. 4,734,262 by Bagshawe. In this device, a non-absorbent seal is provided at the bottom of the well, between the opening in the well and the filter membrane that is combined with an absorbent material. The device is constructed to provide relative movement in the form of reciprocation, between the seal and the opening, but not between the seal and the filter membrane. That is, both the seal and membrane are caused to deflect away from the opening, such as by applying pressure to the top chamber, allowing liquid to pour out onto the filter membrane. Such a construction has several disadvantages. One is that the seal covers the surface of the filter membrane at the tip, thus decreasing the area available for filtration, and most importantly, it prevents the filter from being observed through the opening for a detectable change indicative of a positive reaction. A second disadvantage is a requirement that there be a positive driving pressure to open the seal. This requires an auxiliary instrument, such as a vacuum source, besides what can be done using just the operator's own manipulation.

SUMMARY OF THE INVENTION

I have constructed a diagnostic device with flow control means that avoid the above-noted problems concerning tolerances and difficulties of pressurizing and reading.

More specifically, there is provided a test device useful for conducting a reaction, the device comprising (a) a well configured to confine temporarily a liquid patient sample admixed with at least one reagent, to provide the reaction, (b) a filter at the bottom of the well with pores effective to pass free, unreacted reagent but not complexed or reacted reagent, and (c) an absorbent material underneath the filter effective to draw off liquid in the well after the reaction. The device is improved in that it further includes (d) a non-absorbent pad underneath the filter, adjacent to the absorbent material, and (e) means for moving the filter and the absorbent material relative to each other, and the filter and the pad relative to each other, between two positions, one in which the filter contacts the non-absorbent pad and the other in which the filter contacts the absorbent material.

Accordingly, it is an advantageous feature of the invention that a liquid testing device is provided with a liquid-confining well, a filter, and an absorbent material underneath, that allows flow or no flow of liquid through the filter without the use of vent seals of carefully controlled tolerances.

It is another advantageous feature of the invention that such a liquid testing device is provided that allows filtering of the liquid to occur without having to apply a pressure differential across the filter to open the filter to flow.

It is a related advantageous feature of the invention that such a device is provided wherein the results are easily read from a color change on the filter, after flow is readily initiated by the user.

Other advantageous features will become apparent upon reference to the following Description of the Preferred Embodiments, when read in light of the attached drawings.

BRIEF DESCRIPTION OF THE DRAWINGS

FIGS. 1A and 1B are fragmentary sectional views of a prior art device, requiring a pressure differential to be applied across the filter to cause liquid flow to occur through the filter;

FIG. 2 is a plan view of a device constructed in accord with the invention;

FIGS. 6 and 7 are fragmentary sectional views similar to that of FIG. 3, but illustrating alternate embodiments;

FIG. 8 is a section view taken generally along the line VIII—VIII of FIG. 7.

DESCRIPTION OF THE PREFERRED EMBODIMENTS

Figure 3A:
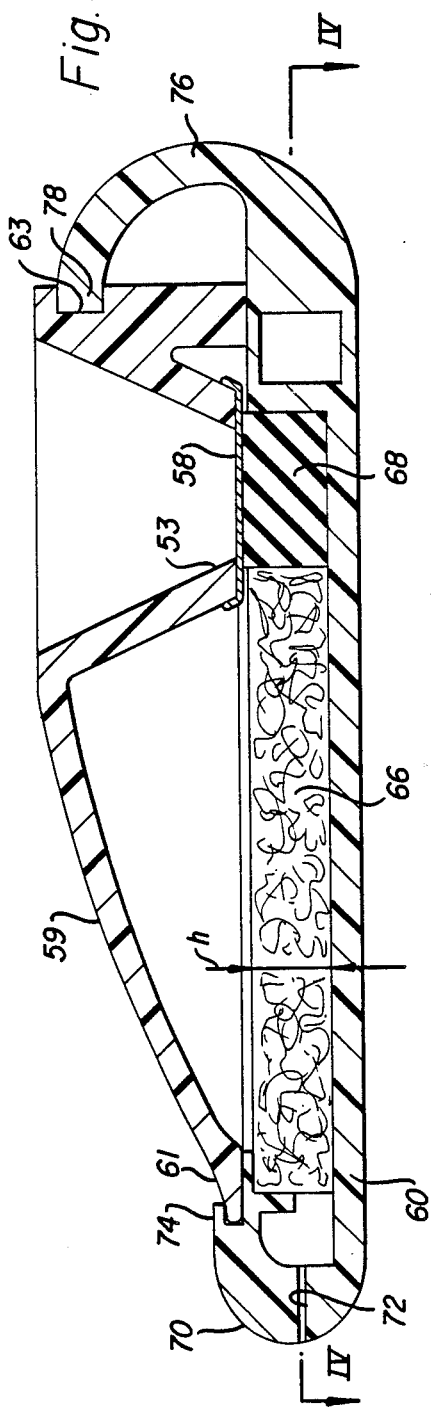
FIGS. 3A and 3B are sectional views of the device of FIG. 2, taken along the line III—III of FIG. 4, with that of 3B being of a slightly different embodiment.

The invention is described herein in the context of the preferred embodiments, in which the device has three pairs of upper/lower compartments, to immunoassay (a) the patient sample, (b) a positive control and (c) a negative control, all more or less simultaneously. The filters are shown as sliding between two positions. In addition, aspects of the invention are useful with only a single pair of compartments, and with any kind of reaction and any form of relative movement between the filter and its absorbent material.

The actual chemistries of the assay are not described in detail, primarily because the mechanics of the device are applicable to any, or even no, chemistry, provided it is appropriate that flow not take place instantaneously into the liquid-receiving compartment.

In the most preferred embodiment, the chemistries provide for an immunoassay, in which there is separately received at three filters in three compartments, a patient antigen complexed with an antigen, a positive control for the complex so formed, and a negative control for the complex so formed, respectively, as is conventional.

FIGS. 1A and 1B illustrate a related device 10 provided by the prior art, specifically one taught by U.S. Pat. No. 4,734,262 noted above. An upper compartment or well 12 has at the bottom of it, an aperture 14 that has mounted below it, a non-absorbent seal 16, that sits on the filter-absorbent material 18 held in place by member 20. Liquid placed in well 12 will not pour into or through material 18 because seal 16 blocks it, FIG. 1A. However, when a differential pressure is applied across material 18, FIG. 1B, such as by a positive pressure applied to well 12 (arrow 22) or a vacuum applied to material 18, both the seal and material 18 pull away from aperture 14 and liquid flow into the filter-absorbent material occurs, arrows 24. As noted above, the disadvantages of such a device are that the presence of seal 16 prevents reading any color change through the top, and it requires the application of a pressure differential to unseat seal 16.

In accordance with the invention, an improved device 50 comprises, FIG. 2, three upper compartments or wells 52a, 52b, and 52c. The bottom 53 of each well, FIG. 3A, is covered with a porous filter 58 which will pass liquid through it unless such flow is blocked either by a liquid lock or some other means. Both the well and its filter are carried on an upper housing 59 having a sloped forward edge 61 and a rear groove 63.

Below housing 59 is a lower housing member 60, FIGS. 2-4, having in an adjacent, and preferably contiguous relationship, both an absorbent material 66 and a non-absorbent seal or pad 68, FIG. 4. The footprint 58 of the filter of each well 52a, 52b and 552c, is shown as contacting pad 68, FIG. 4, before each well moves to where the filter contacts the adjacent absorbent material 66. The height "h", FIG. 3A, of both material 66 and the pad 68 is such as to compress material 66 or pad 68 slightly, when filter 58 contacts either one.

Figure 4:
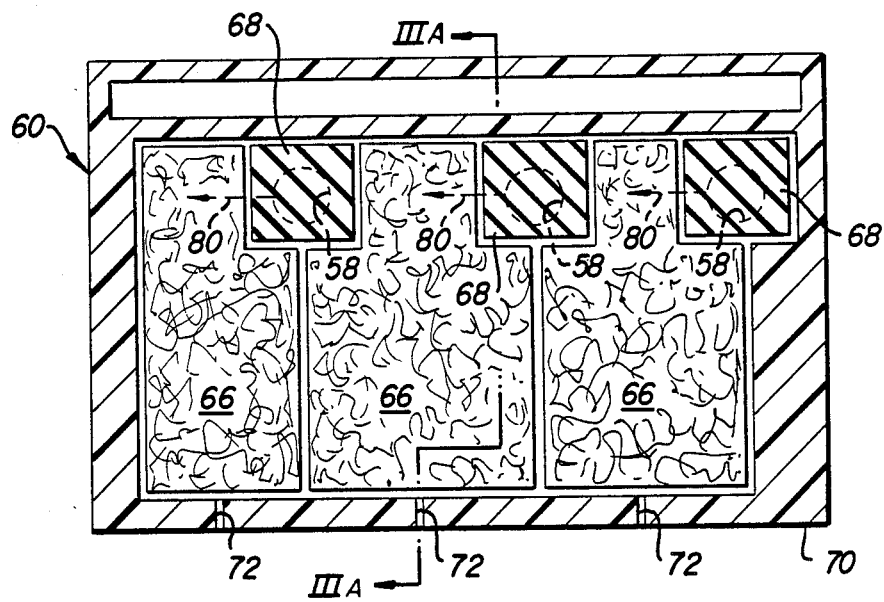
FIG. 4 is a sectional plan view, taken along the line IV—IV of FIG. 3A.

The material 66 and pads 68 are held within lower housing 60, as shown in FIG. 4. Such lower housing has a forward edge 70 that optionally bears one or more vent apertures 72, and a track groove 74, FIG. 3A, that accommodates edge 61 of upper housing 59 in a sliding relationship. Rearward portion 76 of housing 60 has a lip 78 that slidably extends into groove 63. Vertical ribs (not shown) can be located in housing 60 between, e.g., each material 66, to keep them in place.

Thus, as is apparent, upper housing 59 moves relative to lower housing 60 preferably by sliding with respect thereto. This in turn provides a sliding relationship between filter 58 of each well, and both its non-absorbent pad 68 and its absorbent material 66. As shown in FIG. 4, the footprint 58 of the filter (shown in phantom) slides as per arrow 80, from contact with non-absorbent pad 68, to absorbent material 66. That is, each well goes from a non-liquid-flow condition to a liquid-flowing condition, respectively, since apertures 72 insure there is no liquid lock. The word "closed" can be printed at 85 on the top of housing 60, FIG. 2, to inform the user that, when configured as shown in FIG. 2, the wells are closed off from flow. A printing of the word "open" (not shown) is useful at the other end 87 of the top of housing 60.

Other sliding motions are useful as well, for example, one in which the upper housing rotates with respect to the lower housing (not shown).

Yet another useful sliding motion is one in which the lower housing slides relative to the upper housing, which is kept stationary. Such an alternative embodiment appears in FIG. 3B, in which parts similar to those previously described bear the same reference numerals, to which the distinguishing suffix (') (prime) is attached. Thus, device 50' comprises an upper housing 59' and a lower housing 60'. Housing 59' includes wells such as well 52b', and filter 58', and housing 60' houses absorbent material 66' and non-absorbent pad 68', all constructed as described above. However, in this embodiment upper housing 59' remains stationary by reason of its four supports 89 that are attached, for example, at the four corners of such housing. Housing 59' also includes a lip 61' that fits in a groove 74' provided in housing 60', and a rear groove 63' that accommodates lip 78' of housing 60'. Housing 60' is slung to slide within groove 63' and on lip 61' as a track support, in and out of the plane of FIG. 3B.

Useful materials for either embodiment include the following: Filters 58 can be polyamides, such as nylon, and for example nylon-66 microporous membranes manufactured under the tradenames BIODYNE A or ULTRIPOR N-66 by Pall Corporation. Most preferably, the membranes are precoated (prior to use) with one or more water-soluble proteins, such as casein derivatives obtained from acylation, alkylation or sulfonylation of the casein. Various optional additional treatments can be given to the filter upper surface during or before assembly.

Absorbent material 66 can be any bibulous material, having a sufficient pore volume to soak up about 2 cc of liquid. Useful materials include cellulose acetate, cotton, and rayon.

As noted, pads 68 are selected from non-absorbent materials, such as resilient neoprene laminated with a hydrophobic plastic, for example, polypropylene. The resiliency is selected to allow filter 58 to compress pad 68 with sufficient pressure as to withstand about 3 cm of water as a liquid head of pressure, without leaking. Such compression does not significantly interfere with the upper housing 59 being easily slid by a user, relative to lower housing 60, by simply using finger pressure.

As a result, the devices of the invention are particularly useful to provide an immunoreaction within one or all of the wells, between an immunoreagent (such as labeled antibodies) that is pre-applied or added to the well, and the patient's sample. When housing 59 is slid to the open position (by sliding leftward, FIG. 2), the liquid is then free to flow into the absorbent material underneath, carrying with it unreacted (uncomplexed) immunoreagent. However, complexed immunoreagent remains behind on the filter, either because of its size or because a sandwich has formed using beaded antibodies which will not pass through the filter. The labeled antibodies so trapped on the filter are then caused to react to produce a detectable signal.

Figure 5:
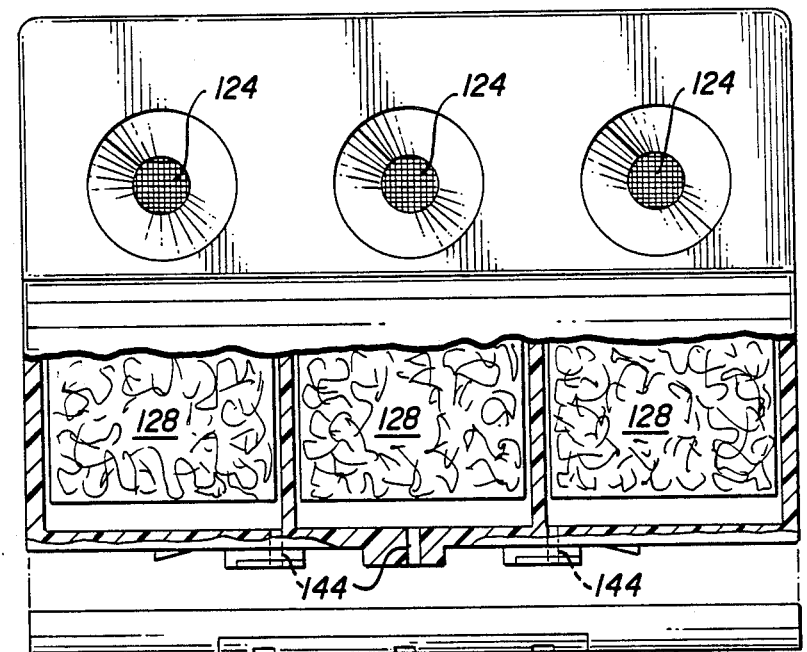
FIG. 5 is an exploded plan view, partially broken away, of a comparative example.

FIG. 5 illustrates a comparative example, wherein no movement occurs between the filter 124 and its absorbent material 128. Instead, those parts occupy a fixed relationship and a slide valve 150 acts to open or close apertures 144, using a compressed elastomeric material inside valve 150 (not shown). Although such a device works well, care is needed in the selection of materials and in the manufacture of related dimensions to insure that valve 150 can be moved by finger pressure. In contrast, less care need be given to the tolerances used to assemble filter 58 of the present invention, in sliding contact with pad 68 or absorbent material 66.

FIG. 6 illustrates another embodiment, in which a rigid non-absorbent pad is used. Parts similar to those previously described bear the same reference numeral to which " is added. Thus, as in the previous embodiment, filter 58″ is mounted over the bottom of each well, such as well 52b″, that is part of upper housing 59″. Housing 59″ slides with respect to lower housing 60″, having in an adjacent configuration, an absorbent material 66″ and a non-absorbent pad 68″ for each well. Unlike the previous embodiment, however, pad 68″ is relatively rigid. To insure that it seats against filter 58″ with sufficient pressure as to prevent leakage, a spring 100 is used to bias pad 68″ upwardly with a force equivalent to about 3 cm of water as a liquid head of pressure. (2.5 cm is the maximum height of liquid used in the wells.) The corners of pad 68″ can be optionally rounded (not shown) to allow filter 58″ to cam pad 68″ down when filter 58″ is moved back over it, if such reasealing is desired.

An example of such a relatively rigid non-absorbent pad 68″ includes a hydrophobic plastic such as polyproplyene.

A rigid non-absorbing pad can be used without the need for a spring 100 that is separate from the rest of the assembly. Such an embodiment is shown in FIGS. 7–9, wherein parts similar to those previously described bear the same reference numeral, to which the distinguishing mark (‴) is appended.

Thus, in FIG. 7, as in the embodiment of FIG. 6, upper housing 59‴ has a well 52b‴ with a filter 58‴, constructed as before. Lower housing 60‴ has both an absorbent material 66‴ and a rigid non-absorbent pad 68‴ with respect to which filter 58‴ slides, also as in the embodiment of FIG. 6. However, in this embodiment the characteristic resilience of material 66‴ is used to bias the rigid pad 68‴ against filter 58‴ with the necessary force. In addition, FIG. 9, material 66‴ has a tendency to protrude at 190 into apertures 200 of pad 68‴, thus providing the desired contiguous location of the absorbent material immediately adjacent to portions 202 of the pad on which the footprint of filter 58‴ presses, FIG. 8. As a result, when well 52a‴ moves as per arrow 204, FIG. 9, it goes from its closed contact with portion 202 of pad 68‴, to the "open" contact with portions 109 of material 66‴.

Figure 9:
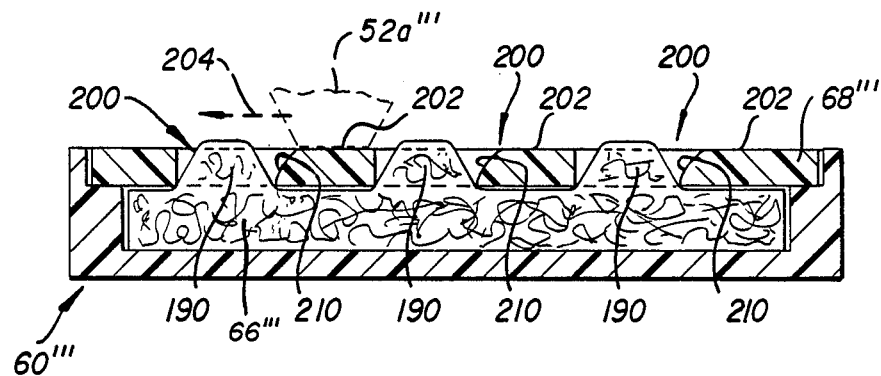
FIG. 9 is a section view taken generally along the line IX—IX of FIG. 8.

Alternatively, material 66‴ can be cut to have the shape shown in FIG. 9 even before pad 68‴ is placed on top of material 66‴.

To allow reclosing of the wells by movement back onto pad 68‴, edges 210 of the portions 202 are preferably beveled.

Figure 3B:
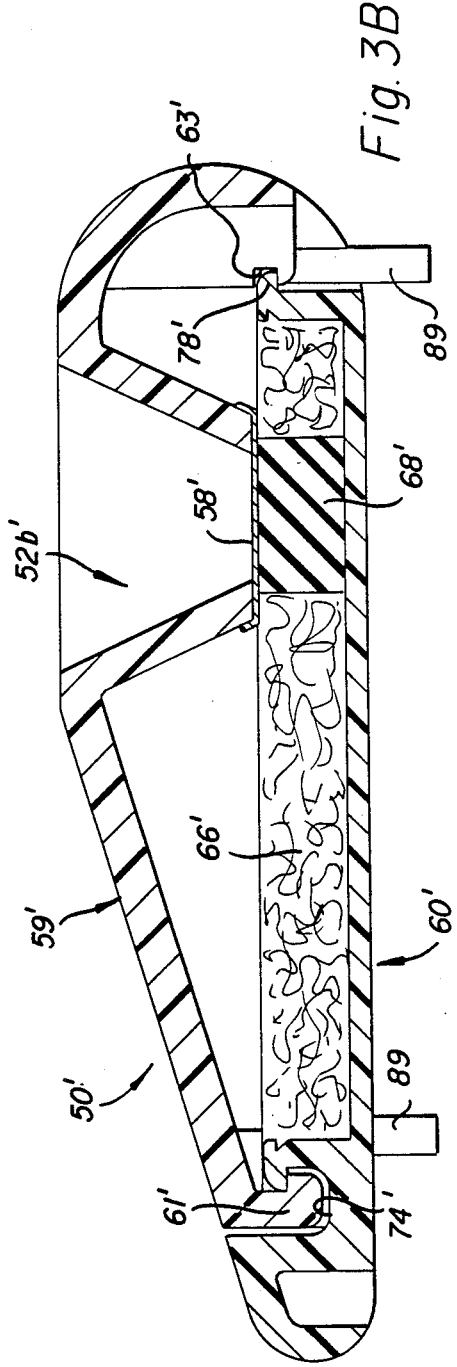

The embodiment of FIGS. 7–9 can also be arranged as shown in FIG. 3B, to provide the relative sliding motion between the two housings.

The invention has been described in detail with particular reference to proferred embodiments thereof, but it will be understood that variations and modifications can be effected within the spirit and scope of the invention.

What is claimed is:

1. In a test device useful for conducting a reaction, said device comprising (a) a well configured to confine temporarily a liquid sample from a patient admixed with at least one reagent, to provide said reaction, (b) a filter at the bottom of said well with pores effective to pass free, unreacted reagent but not complexed or reacted reagent, and (c) an absorbent material underneath said filter effective to draw off liquid in said well after said reaction, the improvement wherein said device further includes (d) a non-absorbent pad underneath said filter, adjacent to said absorbent material, and (e) means for moving both (i) said filter and said absorbent material relative to each other and (ii) said filter and said pad relative to each other, between two positions, one in which said filter contacts said non-absorbent pad and the other in which filter contacts said absorbent material.

2. A device as defined in claim 1, wherein said pad and said absorbent material are stationary within said device, and said filter is mounted for movement between said two positions.

3. A device as defined in claim 2, wherein said moving means comprise means for sliding said filter between said two positions.

4. A device as defined in claim 3, wherein said pad comprises a rigid hydrophobic plastic material, said device further including means for biasing said filter against said rigid material to temporarily seal said filter from liquid flow occurring through the filter.

5. A device as defined in claim 4, wherein said pad rests on a first portion of said absorbent material and exposes a second portion of said absorbent material to contact with said filter, whereby said portion of said absorbent material functions as said biasing means.

6. A device as defined in claim 4, wherein said non-absorbent pad has a beveled surface that facilitates relative movement of said filter and said pad into contacting relationship.

7. A device as defined in claim 3, wherein said pad comprises a resilient hydrophobic plastic material, and wherein said filter is assembled against said material to slidably seal said filter thereagainst with a pressure effective to temporarily prevent liquid flow through the filter.

8. A device as defined in claim 1, wherein said absorbent material and said pad are contiguous.

9. A device as defined in claim 1, wherein said filter is stationary within said device, and said pad and said absorbent material are mounted for movement between said two positions.

10. In a test device for an immunoreaction, said device comprising (a) a well configured to confine temporarily a liquid sample from a patient admixed with at least one immunoreagent, to provide said immunoreaction, (b) a filter at the bottom of said well with pores effective to pass free, unreacted immunoreagent but not complexed immunoreagent, (c) an absorbent material underneath said filter effective to draw off liquid in said well after said immunoreaction, and (d) means for controlling liquid flow from said filter to said absorbent;

the improvement wherein said device further includes a non-absorbent pad underneath said filter, and wherein said liquid-controlling means comprise means for moving both (i) said filter and said absorbent material relative to each other and (ii) said filter and said pad relative to each other, between two positions, to provide contact of said filter with either said non-absorbing pad or said absorbent material, so that proper alternating conditions of no flow or flow occur.

11. A device as defined in claim 10, wherein said pad comprises a rigid hydrophobic plastic material, said device further including means for biasing said filter against said rigid material to temporarily seal said filter from liquid flow occurring through the filter.

12. A device as defined in claim 11, wherein said biasing means includes a portion of said absorbent material.

13. A device as defined in claim 10, wherein said filter is stationary within said device, and said pad and said absorbent material are mounted for movement between said two positions.

* * * * *